(12) United States Patent
Seeh et al.

(10) Patent No.: US 8,251,895 B2
(45) Date of Patent: Aug. 28, 2012

(54) ENDOSCOPE WITH AN ELECTRIC HEATING SYSTEM

(75) Inventors: Daniel Seeh, Immendingen (DE); Armin Pfaff, Seedorf (DE); Norbert Haeckl, Leibertingen (DE); Thomas Weller, Tuttlingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 375 days.

(21) Appl. No.: 12/762,156

(22) Filed: Apr. 16, 2010

(65) Prior Publication Data

US 2010/0268032 A1    Oct. 21, 2010

(30) Foreign Application Priority Data

Apr. 16, 2009    (DE) .................... 10 2009 017 606

(51) Int. Cl.
*A61B 1/00*    (2006.01)
(52) U.S. Cl. .................. 600/169; 600/129; 600/176
(58) Field of Classification Search ............ 600/129, 600/130, 169, 176
See application file for complete search history.

(56) References Cited

U.S. PATENT DOCUMENTS

| 4,076,018 | A | | 2/1978 | Heckele |
| 4,182,547 | A | * | 1/1980 | Siegmund .................... 385/117 |
| 4,722,000 | A | | 1/1988 | Chatenever |
| 4,779,613 | A | | 10/1988 | Hashiguchi et al. |
| 5,533,496 | A | * | 7/1996 | De Faria-Correa et al. .. 128/898 |
| 5,605,532 | A | | 2/1997 | Schermerhorn |
| 5,647,840 | A | * | 7/1997 | D'Amelio et al. ............ 600/169 |
| 5,674,182 | A | | 10/1997 | Suzuki |
| 6,712,479 | B1 | | 3/2004 | Seitzinger et al. |
| 7,938,774 | B2 | * | 5/2011 | Segawa ........................ 600/169 |
| 8,142,351 | B2 | * | 3/2012 | Aono et al. ................... 600/167 |
| 2007/0149856 | A1 | * | 6/2007 | Segawa ........................ 600/169 |
| 2010/0010313 | A1 | | 1/2010 | Muckner et al. |

FOREIGN PATENT DOCUMENTS

| DE | 7440 701 | 4/1975 |
| DE | 37 08 124 A1 | 9/1987 |
| DE | 10 2008 031 881 B3 | 6/2009 |
| EP | 1 803 388 A2 | 7/2007 |
| JP | 2002 291684 A | 10/2002 |
| JP | 2006 000282 A | 1/2006 |

OTHER PUBLICATIONS

Abstract XP002303694, Derwent, Jan. 26, 1987, 1 page.
European Search Report for EP 10153309.9, Jul. 28, 2010, 9 pages.
English translation of European Search Report for EP 10153309.9, Jul. 28, 2010, 8 pages.

* cited by examiner

*Primary Examiner* — John P Leubecker
(74) *Attorney, Agent, or Firm* — Skaar Ulbrich Macari, P.A.

(57) ABSTRACT

An endoscope is provided, comprising a first tube whose distal end is sealed with a cover glass disposed in a mount and an electric heating system for heating the cover glass, with the heating system comprising two electric connections which can be connected with a power source, and an electrically conductive coating which is applied to the inside of the cover glass and comprises two mutually spaced contact sections, of which one each is electrically connected with one of the connections, and with the mount being electrically conductive and a first of the two contact sections being electrically connected via the mount with the associated connection.

9 Claims, 2 Drawing Sheets

ENDOSCOPE WITH AN ELECTRIC HEATING SYSTEM

PRIORITY

The present application claims priority to German Application No. 102009017606.3, filed Apr. 16, 2009, which is hereby incorporated by reference in its entirety.

FIELD

The invention relates to endoscopes, and more particularly, to endoscopes having a heating system to keep the cover glass clear of mist.

BACKGROUND

Endoscopes usually have a tube in which imaging optics are arranged. In order to protect the imaging optics, the distal end of the tube is frequently sealed with a cover glass.

The cover glass can become covered with mist for example when the endoscope, which has room temperature, is inserted into a warmer body cavity.

SUMMARY

It is therefore the object of the invention to provide an endoscope in which the misting of the cover glass can be prevented.

This object is achieved in accordance with certain embodiments of the invention by an endoscope with a first tube whose distal end is sealed with a cover glass disposed in a mount and an electric heating system for heating the cover glass, with the heating system comprising two electric connections which can be connected with a power source and an electrically conductive coating which is applied to the inside of the cover glass and comprises two mutually spaced contact sections, of which one each is electrically connected with one of the connections, and the mount being electrically conductive and a first of the two contact sections being electrically connected via the mount with the associated connection.

The cover glass can be brought to and kept at the desired temperature with the heating system in accordance with the invention. The electrically conductive coating is used as a resistance heating with which a cover glass temperature can be produced in the range of 37° C. to 42° C.

A compact way of making the contact can be realized by allowing the first contact section to make contact via the electrically conductive mount.

The first contact section, in a preferred embodiment, is in direct contact with the mount in order to produce the electric connection of the first contact section with the mount.

The first tube can be electrically conductive in the endoscope in accordance with certain embodiments of the invention and can connect the mount with the connection associated with the first contact section. No additional cabling is thus necessary for making contact with the first contact section.

The mount can be arranged as a separate component which is connected with the first tube. It is also possible to arrange the mount in an integral manner with the first tube, so that the distal end of the first tube forms the mount itself.

Furthermore, a second tube which is electrically conductive can be inserted in the first tube, with an insulating layer being arranged between both tubes. The electric connection of the second contact section with the associated connection occurs via the second tube. Making contact with the conductive coating can thus be realized in a compact way because the tubes that are necessary for the endoscope are used for this purpose.

The two tubes can comprise high-grade steel.

A spring (e.g. a spiral spring) can be arranged between the second contact section and the second tube which produces an electric connection of the second contact section with the second tube. As a result of this kind of contact system, different thermal expansions of the first and second tube can be compensated.

The first tube can be sealed in a hermetically tight way in the endoscope in accordance with the invention. It is understood in this connection that the first tube is capable of autoclaving. In autoclaving, the endoscope or the first tube is subjected for at least several minutes to saturated steam of approx. 120° C. to 140° C. for sterilization without damaging the endoscope (without steam in particular being capable of entering the interior of the first tube). In this case, the endoscope is very inexpensive in medical applications because it can be sterilized in an optimal and very quick manner by autoclaving and can thus be used very frequently.

When seen in a top view of the cover glass, the coating can have the general shape of an open ring. The extension of the coating can thus be chosen as large as possible in order to facilitate the optimal realization of the desired resistance heating.

Imaging optics can be arranged in the endoscope at the distal end in the first tube, which imaging optics are arranged in such a way that for imaging an object disposed in front of the cover glass only light is used which passes through a predetermined partial area of the inside, with the coating outside of the partial area being applied on the inside. As a result, the coating is not arranged in the area (=predetermined partial area) of the inside of the cover glass which is optically used by the imaging optics, so that the coating does not produce any undesirable vignetting.

The cover glass may comprise a sapphire glass.

The endoscope can be arranged as a rigid or flexible endoscope. The endoscope or first tube can be arranged to be bendable. In particular, the distal end of the first tube can be bendable.

The endoscope may comprise a planar image sensor which is arranged after the imaging optics. The image sensor can be arranged in the distal end of the first tube for example. It can also be provided in any other suitable position in the endoscope.

Transfer optics (e.g. relay optics) may be provided between the imaging optics and the proximal end of the endoscope, which transfer optics ensure that the image of the object generated by means of the imaging optics is transferred to the proximal end and can be perceived there by a user for example or can be recorded by means of a video camera provided at the proximal end of the endoscope.

The current or voltage source which can be connected with the two electric connections of the heating system can be a separate source or be integrated in the endoscope. The voltage which is applied by the source between the two connections can be in the range of 0.8 to 1.5 V (especially 1.25 V for example), with a current flowing of approx. 0.5 to 0.9 A (especially 0.75 A).

The coating can be arranged as a metallization. A chromium layer can be provided, for example. In order to achieve optical bonding of the chromium layer on a sapphire cover glass, a silicon oxide layer can be provided between the cover glass and the chromium layer. A gold coating can be arranged in the contact sections instead of the chromium layer or on the chromium layer in order to ensure that contact is made in an optimal fashion.

An antireflective layer (which is obviously not on the contact sections) can also be provided over the entire inside, which is used as a protective layer in the region of the conductive coating and as an antireflective layer for suppressing undesirable scattered light in the remaining area of the inside of the cover glass.

The heating system can comprise a controller with which the current strength flowing through the electric coating can be controlled.

The heating system can further comprise a temperature sensor (e.g. close to the cover glass) with which an actual temperature is detected which is used in feedback control.

The endoscope can have further elements and components known to the person skilled in the art which are necessary for the operation of the endoscope.

It is understood that the features or characteristics of individual embodiments as described herein can also be used in combinations other than explicitly mentioned herein, insofar as it is not stated expressly otherwise. Features of described embodiments can also establish an invention individually.

BRIEF DESCRIPTION OF THE FIGURES

The invention is now explained in closer detail by reference to examples shown in the drawings, wherein.

DETAILED DESCRIPTION

Figure 1:
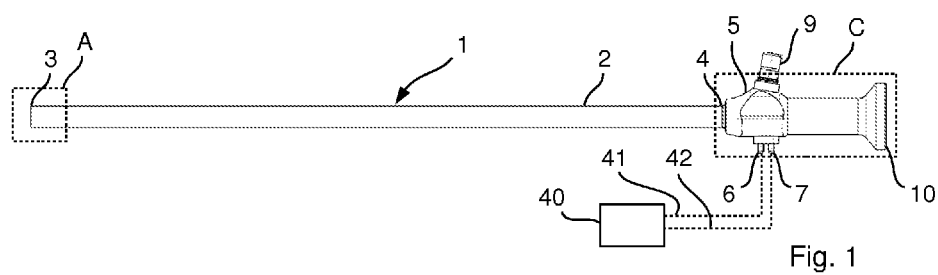
FIG. 1 shows a side view of a first example embodiment of the endoscope in accordance with the invention.

In the example embodiment as shown in FIG. 1, the endoscope comprises a shaft 2 with a distal end 3 and a proximal end 4. The proximal end 4 of shaft 2 opens into a handle which comprises two electric connections 6, 7 of the heating system 8 which will be explained below in closer detail, an optical fiber connection 9 and an ocular opening 10 at the proximal end averted from the shaft 2. The total length of the endoscope 1 as shown in FIG. 1 is approx. 200 mm and the outside diameter of the shaft is approx. 10 mm.

Figure 2:
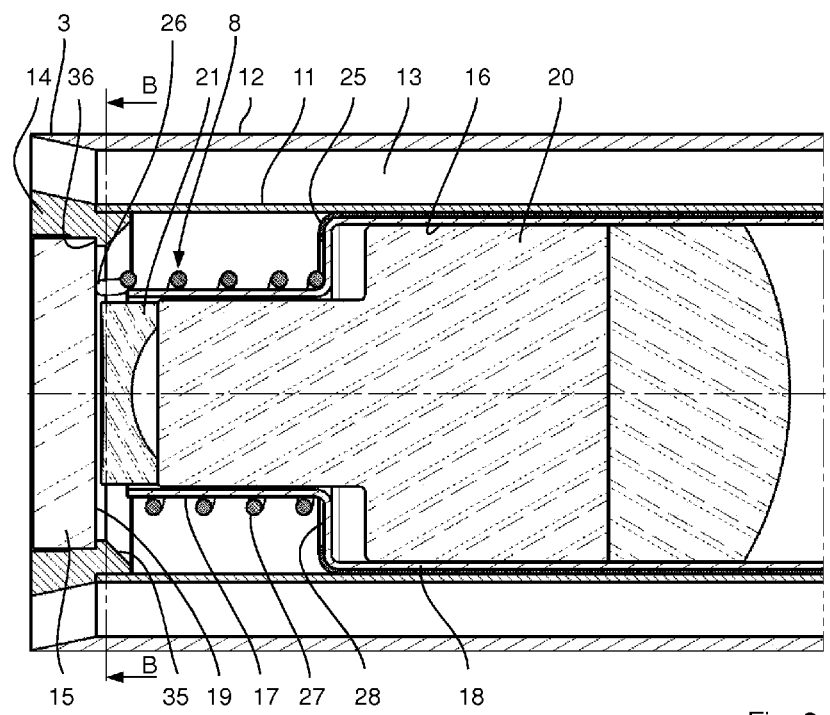
FIG. 2 shows an enlarged sectional view of detail A of FIG. 1.

As can be seen from the enlarged sectional view of detail A of FIG. 1 in FIG. 2, shaft 2 comprises a first tube 11 which is inserted in an outside tube 12 of a larger diameter, so that the intermediate space 13 thus produced between the two tubes 11 and 12 can be used in the known manner for accommodating optical fibers (not shown) which are used for illuminating the object to be inspected.

An electrically conductive mount 14 is fastened to the distal end of the first tube 11, in which a cover glass 15 has been soldered. The connection between the mount 14 and the first tube 11 and between the cover glass 15 and the mount 14 is arranged in such a way that the distal end of the first tube 11 is sealed in a hermetically tight manner.

A second tube 16 is inserted in the first tube 11 which is also electrically conductive and extends from the handle 5 to the distal end 3, with the outside diameter of the second tube 16 from the handle 5 until shortly before the distal end 3 is only slightly smaller than the inside diameter of the first tube 11. An insulating layer 25 is formed between the two tubes 11, 16 which ensures that the two tubes 11, 16 will not touch one another, so that there is no direct electric contact between the two.

As is shown in the illustration of FIG. 2, the second tube 16 comprises a front section 17 whose outside diameter is smaller than the outside diameter of the remaining part 18 of the second tube 16. In the embodiment as shown here, the outside diameter of the front section 17 is smaller by approximately one-third than the outside diameter of the remaining section 18 of the second tube 16. The distal end of the front section 17 is spaced from the inside 19 of the cover glass 15. The same applies to the optics 20 arranged in the second tube 16 because the optical element 21 of optics 20, which is positioned closest to the cover glass 15, is spaced from the cover glass 15. There is thus a gap between the cover glass 15 and the optical element 21.

Figure 3:
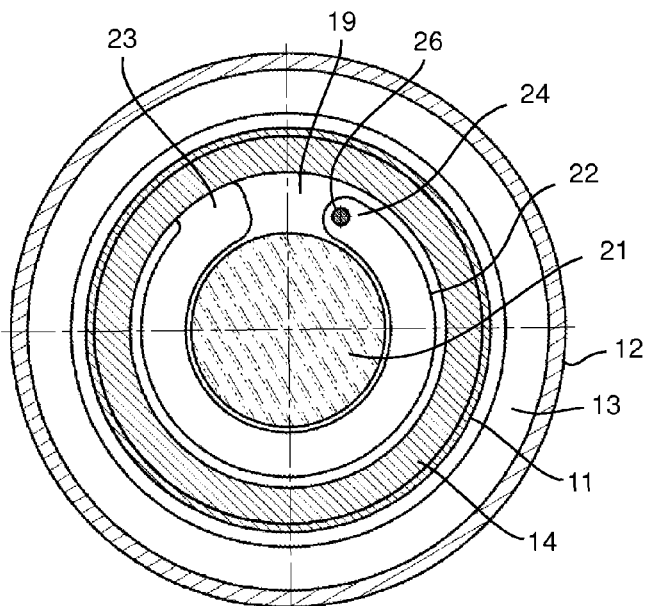
FIG. 3 shows a sectional view along the line B-B in FIG. 2.

FIG. 3 shows a sectional view along the line of intersection B-B of FIG. 2. This sectional view in FIG. 3 shows that an electrically conductive coating or metallization 22 is applied to the inside 19 of the cover glass 15. The coating extends annularly on the inside 19, with the ring form not being completely closed but open. The illustration of FIG. 3 shows clearly that the inside diameter of the coating 22 is larger than the outside diameter of the optical element 21. It can thus be ensured that the coating 22 does not lead to any disadvantageous vignetting for the optics 20 in imaging an object through the cover glass 15.

The coating 22 comprises a first and second contact section 23, 24. The first contact section 23 extends up to the edge of the cover glass 15. Since the cover glass 15 rests with the outer section (which is an annular section here) of the inside 19 on the seat 36 (which is annular in this case) which is formed by a shoulder 35 of mount 14, as is shown especially in FIG. 2, the first contact section 23 is electrically connected with the mount 14.

The front end 26 of a spiral spring 27 rests on the second contact section 24, which spring extends along the front section 17 of the second tube 16 up to a shoulder region 28 of the third tube. The shoulder region 28 connects the front section 17 of the second tube 16 with the remaining section 18 of the second tube 16. The spiral spring 27 is made of an electrically conductive material and/or is coated with such a material and thus makes an electric contact between the second contact section 24 and the second tube 16. By making contact by means of spring 27, the contacting can be ensured even in different temperature-induced expansions of the second and first tube 16, 11.

There is an electric contact between the first contact section 23 and the first tube 11 and between the second contact section 24 and the second tube 16. As already mentioned, the first and second tube 11, 16 are electrically separated from one another by the interposed insulating layer 25.

Figure 4:
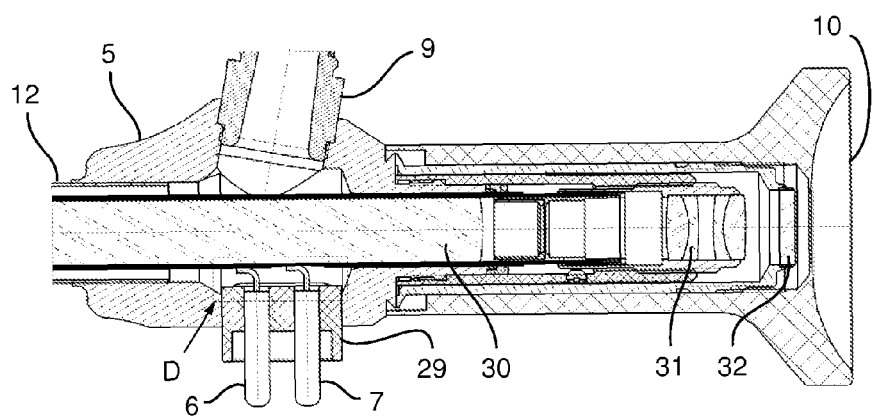
FIG. 4 shows an enlarged sectional view of the detail C of FIG. 1.
Figure 5:
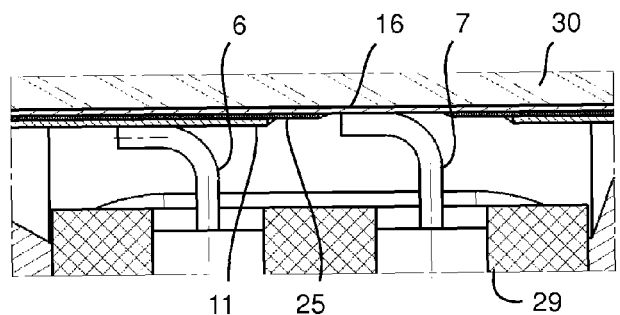
FIG. 5 shows an enlarged view of detail D of FIG. 4.

FIG. 4 shows the detail C of FIG. 1 in an enlarged sectional view. This illustration shows that the first tube 11 is electrically connected with the first electric connection 6. The second tube 16 is electrically connected with the second connection 7. A gap is formed for this purpose in the first tube 11 and the insulating layer 25, as is especially shown in the enlarged view of detail D in FIG. 5, so that the desired electric contact is established between the second tube 16 and the second electric connection 7.

The two connections 6, 7 are held in a connection block (FIG. 4) and are accessible from outside of the endoscope 1. In order to ensure the desired hermetic tightness of the first tube 11, the exposed area is thus sealed with a sealing material (not shown) for example.

The heating system 8 comprises, in the described example embodiment, the two connections 6, 7, the two tubes 11, 16, the interposed insulating layer 25, the mount 14, the metallization 22 and the spring 27. The heating system 8 can further comprise the current or voltage source 40 which is schematically shown in FIG. 1 and which can be connected to the connections 6, 7, as is indicated by the broken lines 41, 42.

When the endoscope 1 is used, an object to be examined (not shown) is transmitted via optics 20 and via rod lenses 30 arranged in the shaft, of which one is shown in FIG. 4, up to the handle 5, in which ocular optics 31 can be arranged, so that the user of the endoscope can perceive the transmitted image of the object via the ocular opening 10. The ocular opening can be sealed by a rear cover glass 32, as is shown in FIG. 4. It is understood that the endoscope 1 can also be arranged in such a way that a video camera can be fastened to the proximal end of handle 5 which records the transmitted image.

The power source 40 is connected to the two electric connections 6, 7, so that there is a current flow from the first electric connection 6 via the first tube 11, the mount 14, the first contact section 23, the coating 22 up to the second contact section 24, the spring 27, the second tube 16 up to the second electric connection 7 (or vice-versa). The current flow is set in such a way that as a result of the resistance of the coating 22, heating of the cover glass 15 is ensured in order to prevent undesirable misting of the cover glass 15. The current flow can be set in such a way for example that the cover glass is heated to approx. 40° C. For this purpose, the current strength is 0.75 A at an applied voltage of 1.25 V.

It is understood that the supply with current can be performed in a controlled manner. It is further possible to provide a temperature sensor in the region of the cover glass 15 in order to perform feedback control to an adjustable desired temperature value.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. An endoscope, comprising:
   a first tube, including a distal end sealed with a cover glass disposed in a mount; and
   an electric heating system for heating the cover glass, the heating system comprising:
   first and second electric connections configured for connection with a power source; and
   an electrically conductive coating applied to the inside of the cover glass, the electrically conductive coating comprising first and second mutually spaced contact sections,
   wherein the first contact section is electrically connected to the first electric connection and the second contact section is electrically connected to the second electric connection,
   and wherein the mount is electrically conductive and the electrical connection between the first contact section and the first electric connection is via the conductive mount.

2. An endoscope according to claim 1, wherein the first tube is electrically conductive and wherein the electrical connection between the mount and the first electric connection is via the conductive first tube.

3. An endoscope according to claim 1, further comprising:
   an electrically conductive second tube disposed in the first tube: and
   an insulating layer disposed between the first and second tubes,
   wherein the electrical connection of the second contact section with the second electric connection is via the conductive second tube.

4. An endoscope according to claim 3, further comprising a spring disposed between the second contact section and the second tube, wherein the second contact section is electrically connected to the second tube via the spring.

5. An endoscope according to claim 1, wherein the first tube is hermetically sealed.

6. An endoscope according to claim 1, wherein the coating generally comprises an open ring when the cover glass is seen in a top view.

7. An endoscope according to claim 1, further comprising imaging optics disposed in the first tube at the distal end, the imaging optics configured such that imaging an object disposed in front of the cover glass uses only light, which passes through a predetermined partial area of the inside of the cover glass, with the coating outside of the partial area being applied on the inside of the cover glass.

8. An endoscope according to claim 1, wherein the coating includes metal.

9. An endoscope according to claim 1, wherein the first contact section is electrically connected directly to the mount.

* * * * *